United States Patent [19]

Donachy et al.

[11] 4,222,127

[45] Sep. 16, 1980

[54] BLOOD PUMP AND METHOD OF PUMPING BLOOD

[75] Inventors: James H. Donachy, Annville; William S. Pierce, Hummelstown, both of Pa.

[73] Assignee: Donachy and Pierce, Hummelstown, Pa.

[21] Appl. No.: 912,033

[22] Filed: Jun. 2, 1978

[51] Int. Cl.³ .......................... A61F 1/24; A61M 1/03
[52] U.S. Cl. ....................................... 3/1.7; 128/1 D; 417/384; 417/394; 417/474
[58] Field of Search ............. 3/1.7; 128/1 D, DIG. 3; 417/383, 384, 394, 395, 474, 412, 413

[56] References Cited

U.S. PATENT DOCUMENTS

| | | | |
|---|---|---|---|
| 3,327,322 | 6/1967 | Norton | 3/1.7 |
| 3,406,633 | 10/1968 | Schomburg | 417/394 |
| 3,425,064 | 2/1969 | Carnevale et al. | 3/1.7 |
| 3,518,702 | 7/1970 | LaRussa | 3/1.7 |
| 3,755,825 | 9/1973 | DeBakey et al. | 3/1.7 |
| 3,766,567 | 10/1973 | Kahn et al. | 3/1.7 |
| 3,771,173 | 11/1973 | Lamb, Jr. | 3/1.7 |
| 3,783,453 | 1/1974 | Bolie | 3/1.7 |
| 3,842,440 | 10/1974 | Karlson | 3/1.7 |
| 3,919,722 | 11/1975 | Harmison | 3/1.7 |
| 3,974,825 | 8/1976 | Normann | 3/1.7 X |
| 4,078,267 | 3/1978 | Cieszynski | 3/1.7 |

OTHER PUBLICATIONS

"Criteria for Human Total Artificial Heart Implantation based on Steady State Animal Data", by R. K. Javik et al., Trans. American Society for Artificial Internal Organs, vol. XXIII, 1977, pp. 535–542.

"The Artificial Heart", by William S. Pierce et al., Reprint from the Archives of Surgery, vol. 112, Dec. 1977, pp. 1430–1438.

"Prolonged Mechanical Support of the Left Ventricle", by William S. Pierce et al., Presented at American Heart Assn. Meeting, Nov. 1977 Published in Circulation, Supp. 1, vol. 58, No. 3, Sep. 1978.

Polymers in Biomedical Devices: Materials for Artificial Heart and Circulatory Assist Devices, by W. S. Pierce, Reprint from Polymers in Medicine and Surgery, 1974, pp. 263–285.

"Assisted Circulation, The Mechanical Heart", by Lawrence S. Cohen, Thoracic and Cardiovascular Surgery with Related Pathology, Third Edition–William W. L. Glenn et al., 1975, pp. 1206–1222.

"Status of the Artificial Heart and Cardiac Assist Devices in The United States", by W. J. Kolff et al., Transactions Amer. Soc. Artificial Internal Organs, vol. XXI, 1975, pp. 620–638.

"A Comparison of Three Ventricles Used for Left Ventricular Bypass in the Calf", by W. O'Bannon et al., Transactions Amer. Soc. Artificial Internal Organs, vol. XXII, 1976, pp. 450–458.

"Complete Left Ventricular Bypass with a Paracorporeal Pump", by W. S. Pierce et al., Reprint from Annals of Surgery, vol. 180, No. 4, Oct. 1974, pp. 418–426.

"Development of Fabrication Techniques for Use of Thermoplastic Polyurethanes in Cardiac Assist and Support Devices", by D. R. Owen et al., Proceedings of The National Technical Conference Society of Plastics Engineering, Nov. 8–10, 1977, Denver, Colorado, pp. 10–15.

"Thrombus Generation Within the Artificial Heart", by D. B. Olsen et al., The Journal of Thoracic & Cardiovascular Surgery, vol. 70, No. 2, Aug. 1975, pp. 248–254.

*Primary Examiner*—Ronald L. Frinks
*Attorney, Agent, or Firm*—Thomas Hooker

[57] ABSTRACT

A blood pump for implant or paracorporeal use having a rigid case with inlet and outlet valves defining a pumping cavity; an integral thin walled flexible sac freely confined within a pumping cavity; and a flexible diaphragm within the cavity conforming to the shape of the adjacent side of the sac. The case includes a control ring projecting into the cavity between the diaphragm and sac. The diaphragm is moved between diastolic and systolic positions to pump blood through the valves. During pumping, the ring distributes flexing of the diaphragm over an increased area while also preventing the interior walls of the sac from contacting each other. The outlet port and the portion of the sac immediately surrounding the outlet port are less flexible than the remainder of the sac away from the port and the portion of the diaphragm overlying the outlet port is less flexible than the remainder of the diaphragm. The less flexible portions of the sac and diaphragm improve pressure pulse pumping so that the more flexible portion of the sac away from the outlet port is initially collapsed and the sac is progressively collapsed from that portion to the outlet port to minimize stasis in the pumping chamber. The less flexible portion of the sac also prevents collapse at the port due to the decreased Venturi effect pressure during the systolic stroke.

43 Claims, 17 Drawing Figures

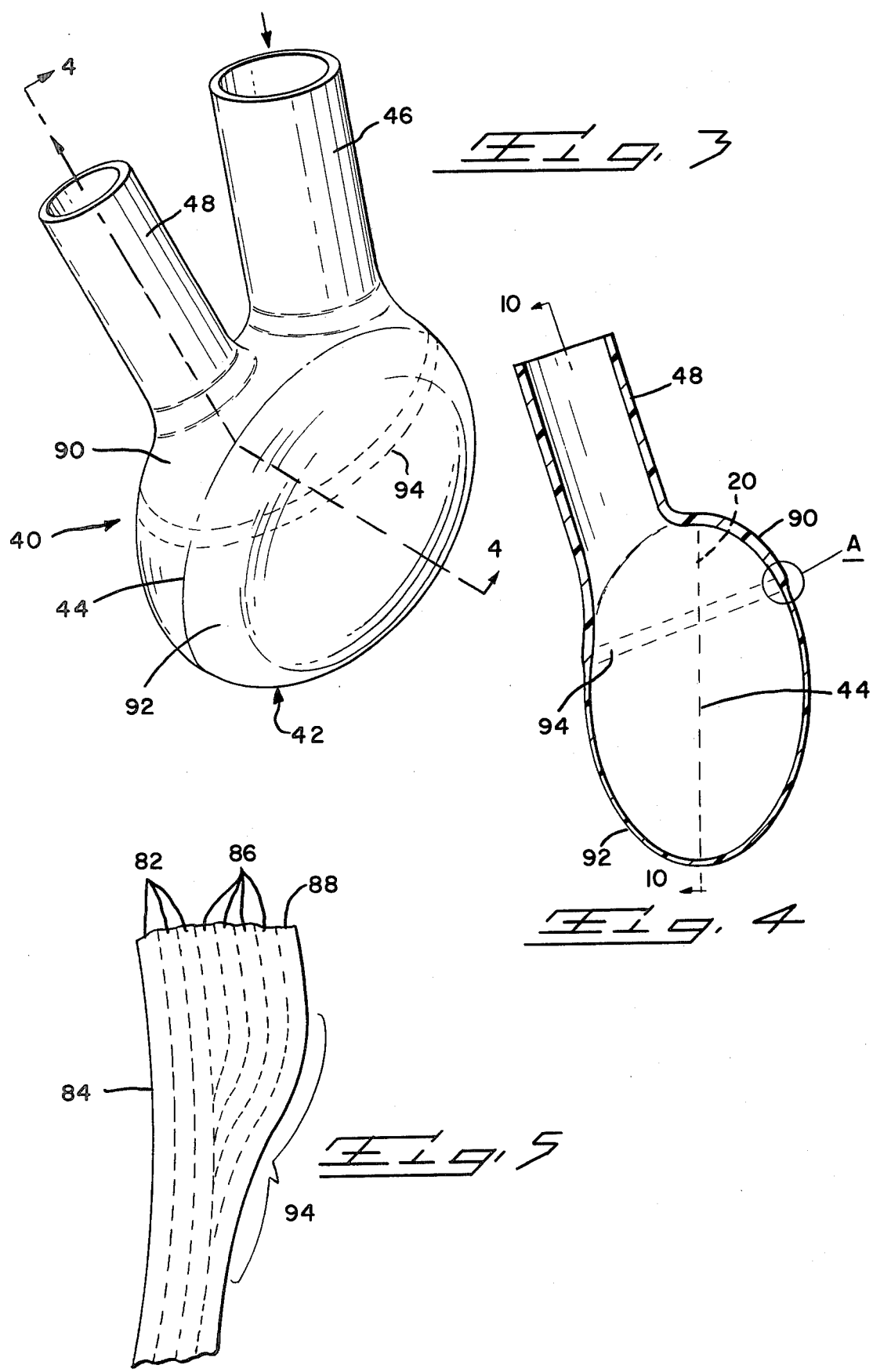

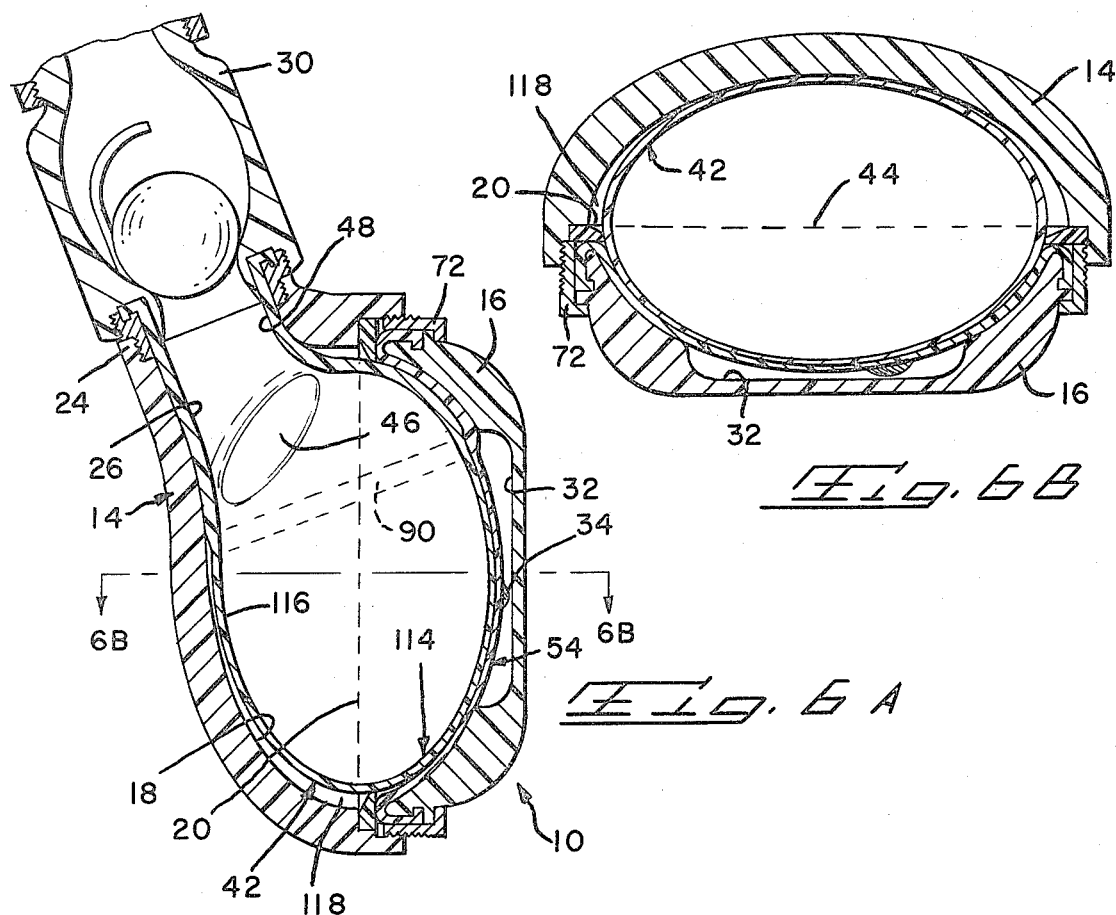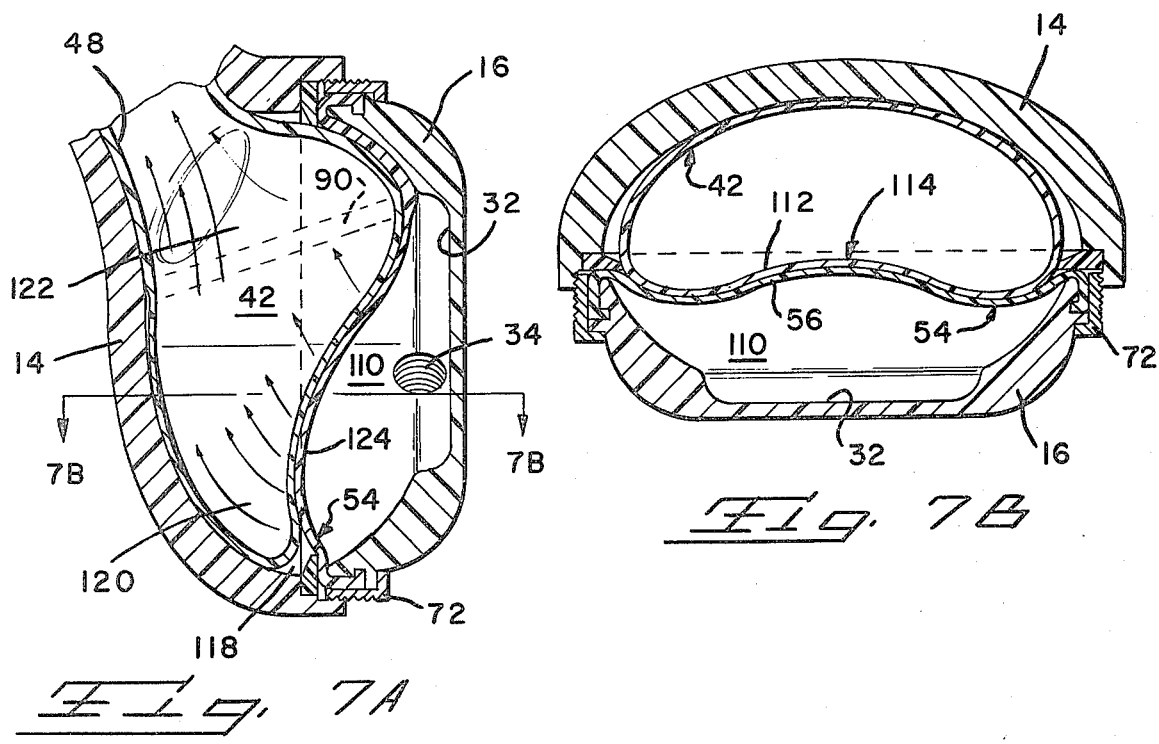

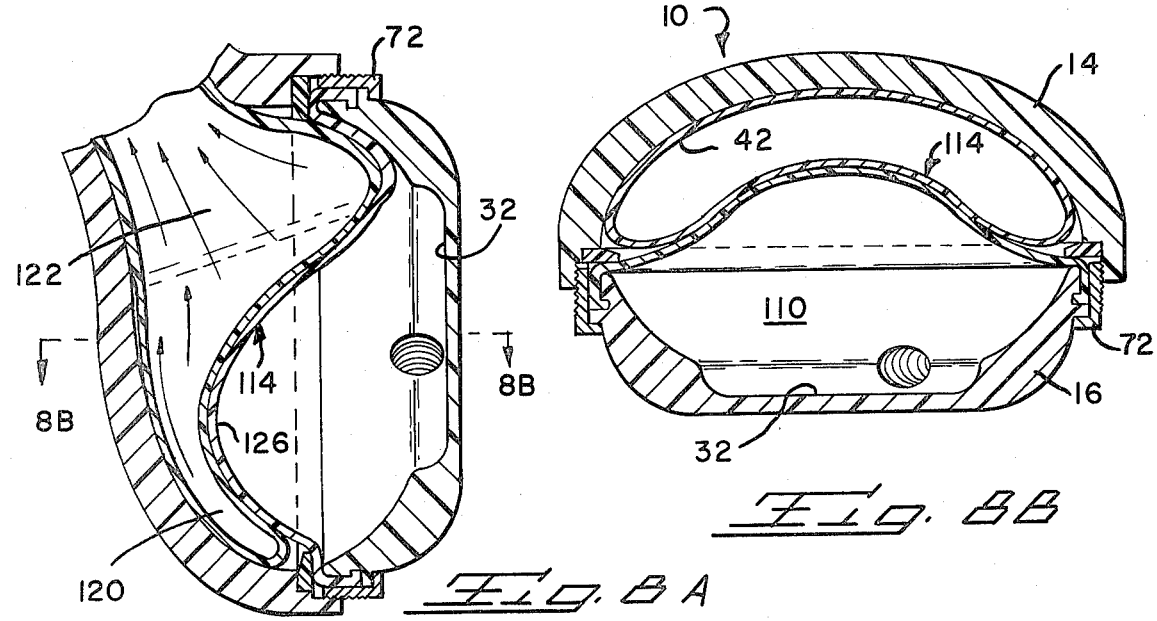
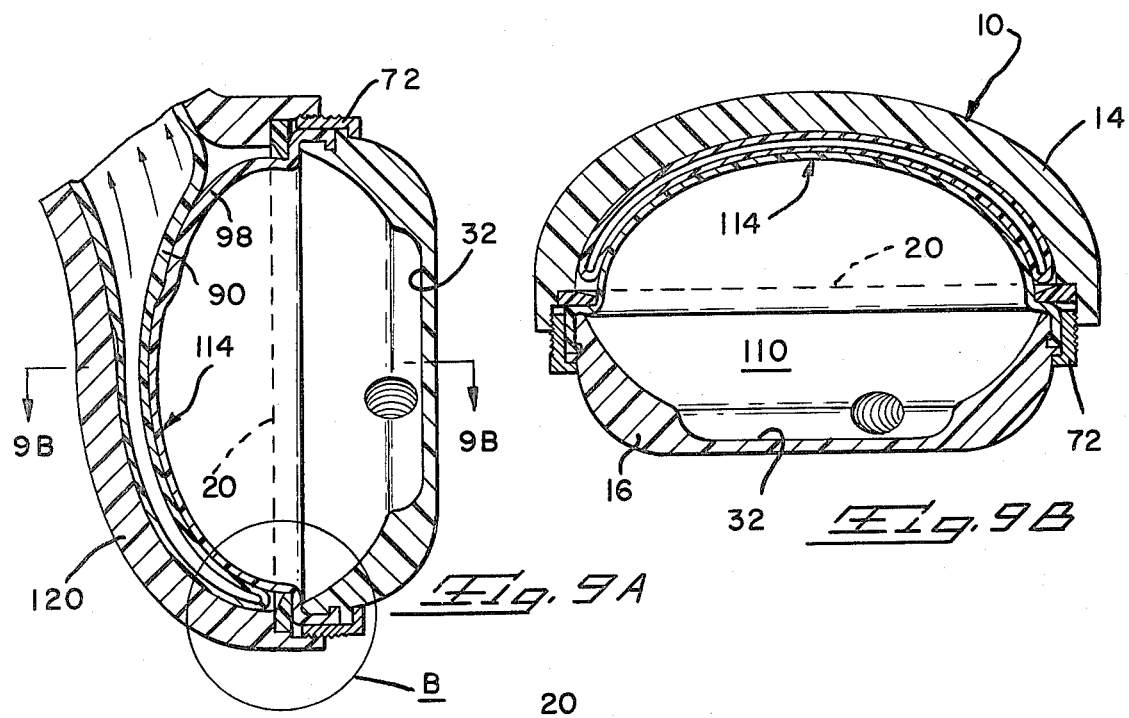
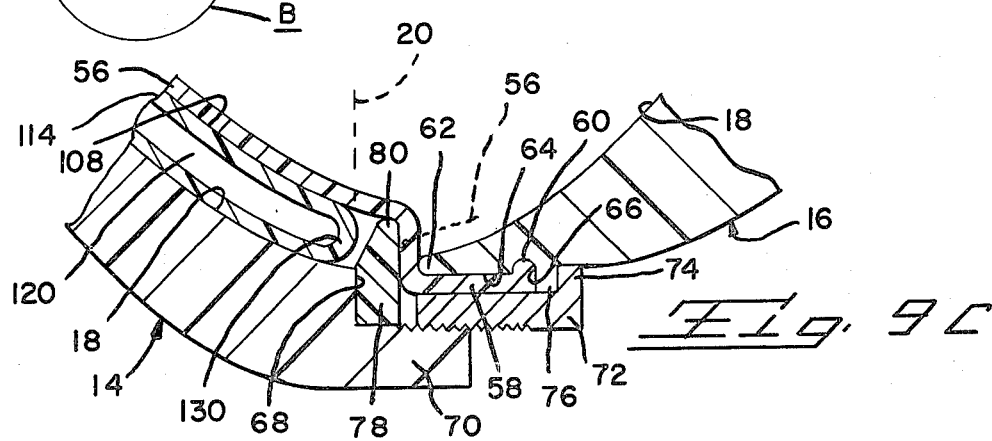

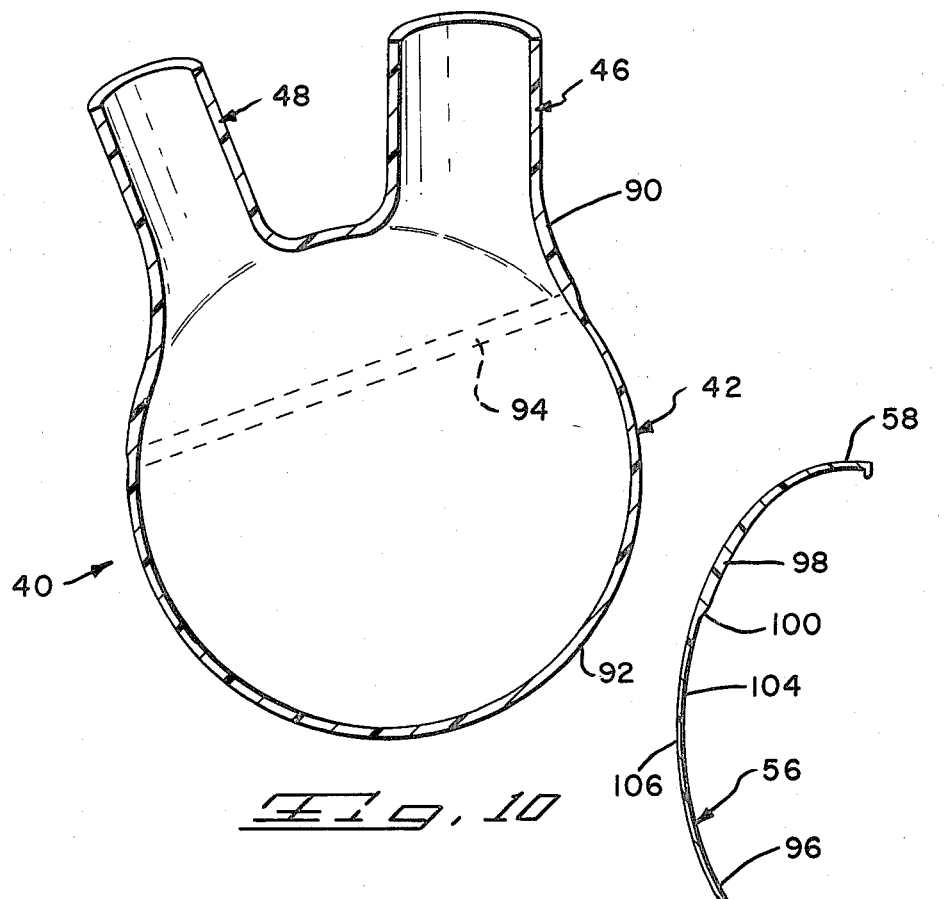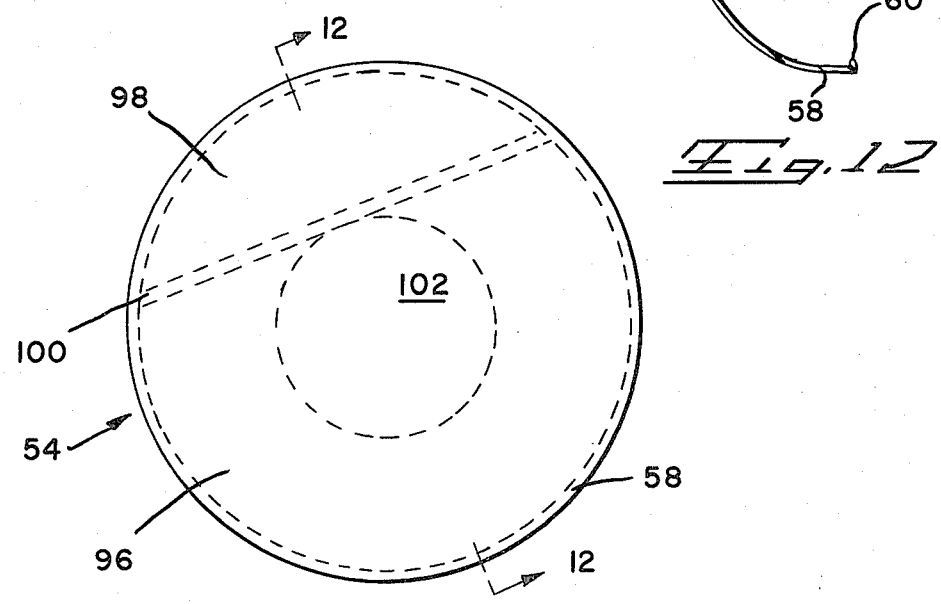

BLOOD PUMP AND METHOD OF PUMPING BLOOD

The invention relates to an artificial blood pump closely simulating the action of the natural heart. Single blood pumps can be used to replace individual ventricles, more commonly the left ventricle, and pairs of blood pumps may be used to replace an entire heart. The blood pump may be used paracorporeally with extended cannulae connected to the circulatory system, or alternatively may be implanted within the thoracic cavity. The blood pump has an extended useful life over conventional pumps with minimum hemolysis and thrombus formation.

In recent years increasing effort has been expended in the development of an artificial blood pump capable of assisting or replacing a failing heart.

An initial goal was to develop an artificial heart sufficiently reliable and noninjurious to the blood to be used to support a patient during relatively short recuperatory periods. The ultimate goal was to develop a noninjurious reliable heart which could be used to support a patient long term. Preferably this heart would be implanted within the thoracic cavity.

Research has resulted in a number of proposed artificial hearts. These artificial hearts, while capable of pumping blood for an initial period, have been unsatisfactory for a number of reasons. Flexible pumping walls are exposed to localized stresses during the pumping cycle and rupture upon prolonged use. Clots form within the pumping chamber of the heart and may be dislodged and pumped from the heart into the circulatory system. In many proposed artificial hearts, the pumping stroke physically injures blood cells, thus decreasing the ability of the blood to support living tissue. Further, many of the conventional artificial hearts are bulky and unsuitable for implantation within the thoracic cavity. Obviously, these defects seriously limit the usefulness of an artificial heart.

Blood pumps have been proposed where the pumping chamber is a continuous integral member extending to the inlet and outlet valves. Blood pumps using pumping sacs are disclosed in U.S. Pat. Nos. 3,425,064; 3,755,825; 3,518,702; 3,771,173 and 3,842,440. Sac-type blood pumps are shown in Pierce, *Polymers in Biomedical Devices: Materials for Artificial Heart and Circulatory Assist Devices,* pp. 263–286, Polymers in Medicine and Surgery, Plenum Publishing Corp., 1974 and Pierce, et al, *Complete Left Ventricular Bypass With a Paracorporeal Pump: Design and Evaluation,* pp. 418–426, Annals of Surgery, Vol. 180, No. 4, October 1974.

Our improved blood pump is of the sac-type and uses a continuous semiellipsoidal pumping sac confined without physical attachment within a semiellipsoidal pumping cavity. The inlet and outlet ports are located adjacent each other immediately on one side of the sac and cavity equators. A domed pumping diaphragm extends into the cavity on the side of the equator away from the inlet and outlet ports and conforms the shape to the adjacent side of the sac. During pumping, the diaphragm and adjacent side of the sac move back and forth together between the diastolic and systolic positions. Preferably, this motion is in response to pressure and vacuum pulses applied to the space between the diaphragm and the adjacent wall of the pumping chamber.

An inwardly projecting control ring extends into the pumping cavity between the equator and the diaphragm. The ring controls flexing of the diaphragm and distributes flexing stresses over an increased area extending inwardly a distance equal to the inward extent of the ring. The ring also aids in assuring that the sac is not completely collapsed in the systolic position.

The diaphragm and ring control the collapse of the sac to assure a high ejection fraction with the walls of the sac being brought very close to each other without contacting each other. Stagnation is reduced without hemolysis. In the systolic position the wall of the pumping sac adjacent the diaphragm is flexed into the pumping chamber about a smooth 180° bend at approximately the sac equator. The ring spaces the diaphragm outwardly from the pumping wall chamber to provide room for the bend and assures that the diaphragm doe not press the sac against the chamber wall and form a sharp crease. Such a crease would undesirably stress the sac and lead to stress fracture after protracted pumping.

The sac is preferably formed from a number of integral layers of segmented polyurethane and is freely confined within the pumping chamber. The ends of the sac inlet and outlet ports away from the pumping chamber are connected to the inlet and outlet valves and form the only physical connections between the sac and the case. The diaphragm and pumping cavity conform to the shape of the sac so there is no need for a physical connection between the sac and these members in order to hold the sac in the proper pumping position. The connections joining the sac inlet and outlet ports to the respective inlet and outlet valves are away from the pumping cavity and do not materially affect the pumping operation.

In this way, the sac is free of restraining appendages or other integral attachments which we have found change the properties of the sac material at the inner blood contacting surface and lead to thrombus formation on the inner surface of the sac. Appendages as used in other blood pumps also tend to increase flexing stresses in the sac wall which ultimately reduce the useful life of the sac. The smooth integral appendage free sac is easier to manufacture than sacs having more complicated shapes.

During the systolic stroke blood is ejected from the pump through the outlet port and outlet valve at a high velocity thereby reducing the pressure in and around the outlet port. Collapse of the sac and obstruction of the outlet port because of the reduced Venturi effect pressure is prevented by making the sac thicker at the port and immediately surrounding the port. The diaphragm may also have a thicker less flexible portion above the outlet port.

The thicker less flexible portions of the sac and diaphragm also assure that the more flexible portions of the sac and diaphragm away from the outlet port collapse first to eject blood from lower portion of the sac prior to collapse of the sac adjacent the outlet port. In this way, the pump assures good blood washout, minimum stagnation and reduced thrombus formation.

Accordingly, an object of our invention is to provide an improved artifical blood pump and improved method for pumping blood.

Another object is to provide a blood pump with an improved useful life with minimum hemolysis and thrombus formation.

A further object is to provide a sac-type blood pump driven by a diaphragm with a control ring to distribute stresses on the diaphragm and to prevent creasing of the sac.

A further object is to provide a sac-type blood pump where the sac at and adjacent the outlet port is less flexible than the remainder of the sac to control collapse of the sac during the systolic stroke;

A further object is to provide an improved pumping sac for use in an artificial blood pump;

A still further object is to provide a pumping diaphragm for use in an artificial blood pump;

Other objects and features of the invention will become apparent as the description proceeds, especially when taken in conjunction with the accompanying drawings illustrating the invention, of where there are five sheets.

In the Drawings:

FIG. 3 is a perspective view of a pumping sac as used in the invention;

FIG. 4 is a sectional view taken generally along line 4—4 of FIG. 3;

FIG. 5 is an enlarged view of portion A of FIG. 4;

FIGS. 6A, 7A, 8A and 9A are sectional views taken generally along section lines 6A—6A of FIG. 1 illustrating the movement of the sac and diaphragm from the diastolic position of FIG. 6A to the systolic position of FIG. 9A;

FIGS. 6B, 7B, 8B and 9B are sectional views taken, generally along lines 6B—6B, 7B—7B, 8B—8B, and 9B—9B of FIGS. 6A, 7A, 8A and 9A;

FIG. 9C is an enlarged view of portion B of FIG. 9A;

FIG. 10 is a sectional view taken, generally, along line 10—10 of FIG. 4;

FIG. 11 is a plan view of the diaphragm removed from the pump; and

FIG. 12 is a sectional view taken along line 12—12 of FIG. 11.

Figure 1:
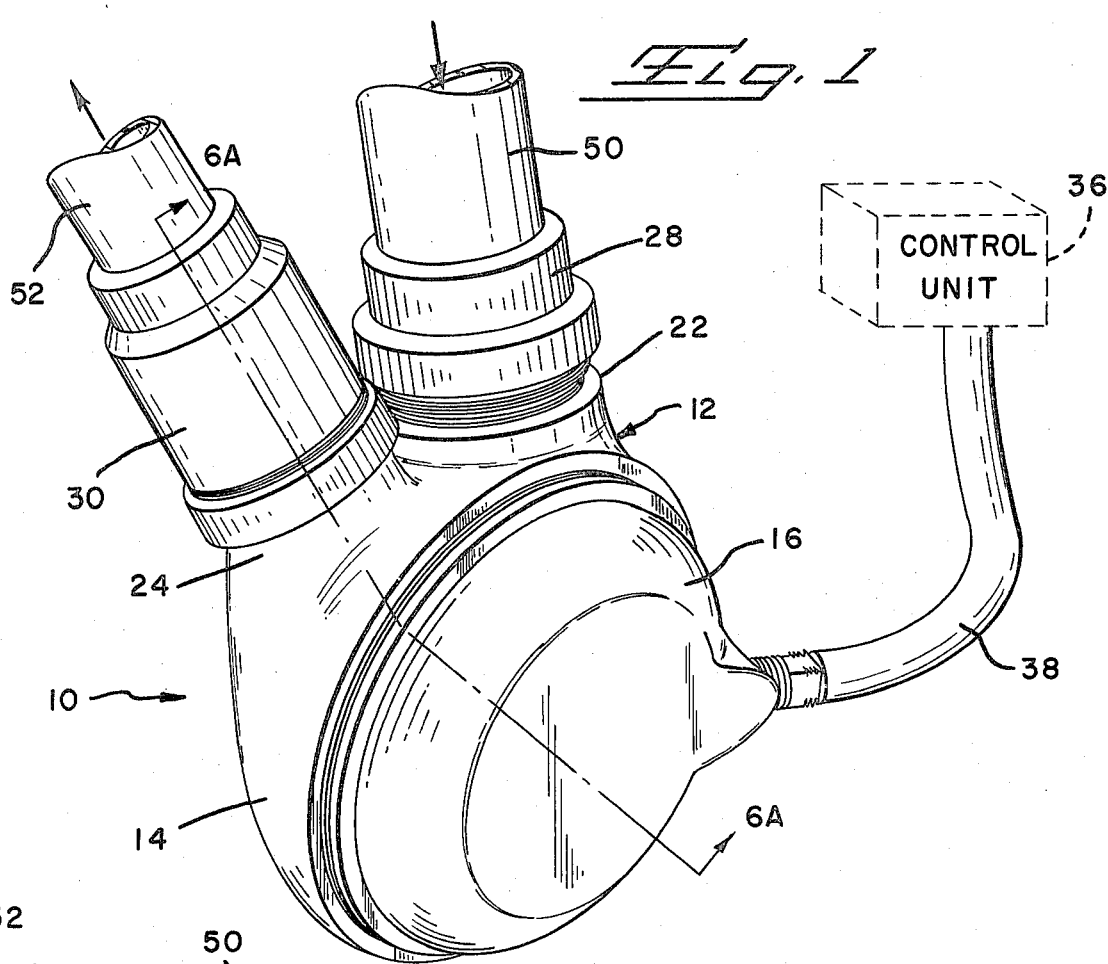
FIG. 1 is a perspective view of a blood pump and a control unit according to the invention.
Figure 2:
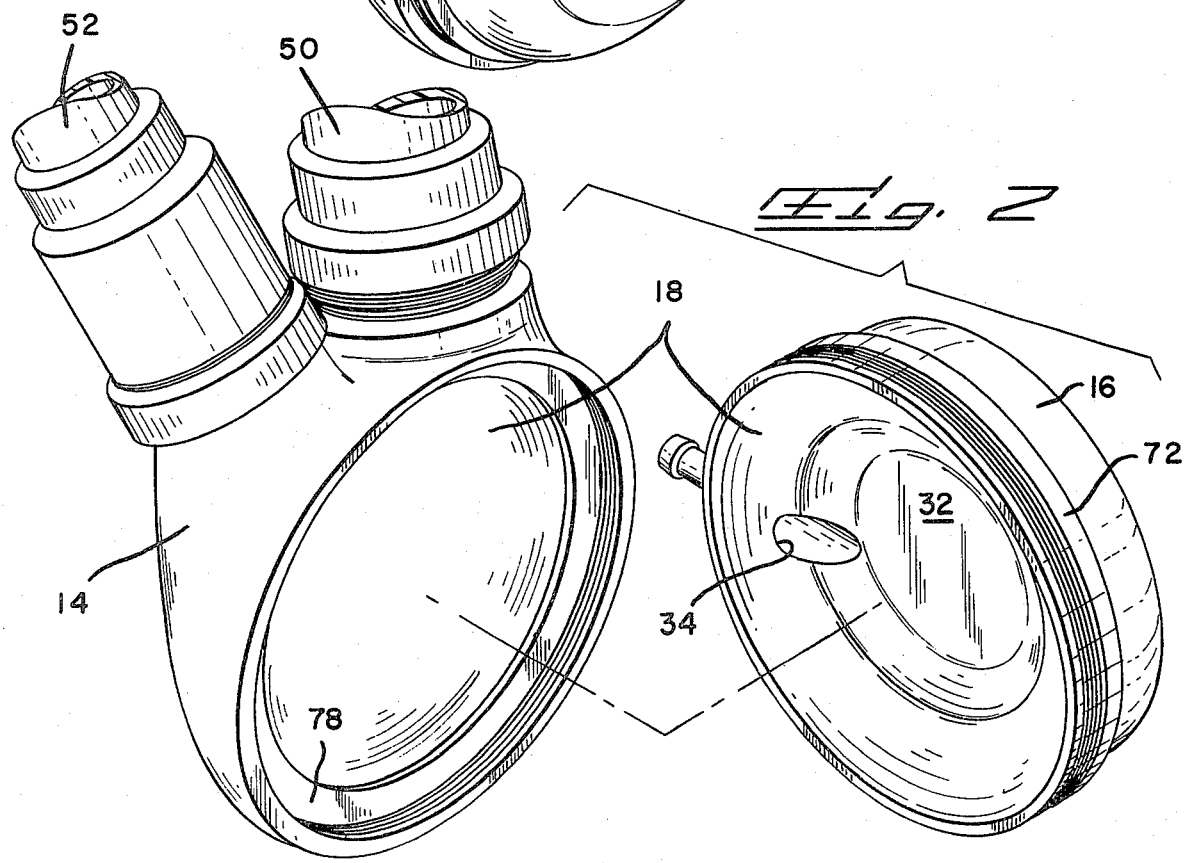
FIG. 2 is an exploded view of the base and cover of the pump with the sac and diaphragm removed.

Blood pump 10 has a rigid case 12 made up of base 14 and cover 16. When assembled, the base and cover define a generally ellipsoidal interior pumping cavity 18 having an equator indicated by line 20. Inlet and outlet necks 22 and 24 extend from one side of the cavity in base 14 and define an inlet passage (not illustrated) and an outlet passage 26 both communicating with the interior of the pumping cavity. The inlet and outlet passages intersect the pumping cavity 18 adjacent each other at the top of the pump and close by and to one side of the equator 20. A suitable inlet valve 28 is attached to the end of neck 22 and a suitable outlet valve 30 is attached to the end of neck 24. As in a natural heart, the diameter of the inlet passage is greater than the diameter of the outlet passage.

Cover 16 includes a central pumping recess 32 formed in the wall of the cavity 18 away from the equator 20. A pressure passage 34 opens into recess 32 and is connected to control unit 36 by suitable conduit 38. Unit 36 is commercially available and forms no part of the invention.

A thin walled flexible pumping sac 40 illustrated in FIGS. 3, 4, 5 and 10 is confined within the pumping cavity and is deformed in a controlled manner to pump blood past the valves 28 and 30. The sac 40 includes a generally ellipsoidal blood pumping chamber 42 fitted within the pumping cavity 18. Equator 44 of chamber 42 lies in the plane of cavity equator 20 when the sac is in the diastolic position of FIGS. 6A and 6B. Both equators are preferably circular in shape. The sac also includes integral inlet port 46 and outlet port 48 which extend through the respective inlet and outlet passages in necks 22 and 24. The ends of both the inlet and outlet ports are clamped between parts of their respective inlet and outlet valves 28 and 30 to form fluid tight connections between the sac and the interior of the valves.

A single pump 10 may be used to provide either left or right ventricular assist. When used as a left ventricular assist, as shown in FIG. 1, cannula 50 connects the ventricle to inlet valve 28 and cannula 52 connects the outlet valve 30 to the aortas. Pairs of pumps 10 may be used as total heart replacements. The single pump or pairs of pumps may be implanted within the thoracic cavity or may be located paracorporeally and connected to the patient through cannulae extending into the cavity.

The pumping chamber 42 is expanded and collapsed by movement of domed diaphragm 54 illustrated FIGS. 11 and 12. The diaphragm includes a domed generally semiellipsoidal pumping wall 56 with a cylindrical retaining lip 58 extending around the periphery of the wall and carrying an inwardly facing retaining bead 60. The open side of cover 16 includes a rounded circular edge 62 joining outwardly facing cylindrical sidewall 64. A bead groove 66 is formed in the edge of sidewall 64 away from edge 62. The diaphragm 54 is fitted on the cover 16 with the inner surface of lip 58 on side 64 and with bead 60 in groove 66. The domed pumping wall 56 covers the part of the pumping cavity 18 formed within the cover so that pressure and vacuum pulses generated by control 36 serve to expand and collapse the diaphragm.

As shown in FIG. 9C, the interior surface of pumping cavity 18 in base 14 extends to the equator 20. A circumferential notch 68 on the equator 20 extends radially outwardly from the intersection of surface 18 to the inner side of cylindrical wall 70. This surface is suitably threaded.

A flat circular control ring 78 is seated against notch 68 so that it lies on the cover side of the equator 20.

The cover is secured to the base by means of metal retaining ring 72 having threads on the outer surface thereof and an inwardly extending stop shoulder 74. The ring has a close fit around the outer circumference of the cover 16 with shoulder 74 engaging edge 76. The ring is threaded into the base as shown in FIG. 9C. When in this position, the cover lip 62 sandwiches the diaphragm against ring 78 as illustrated.

The side of the ring 78 away from the equator extends into the pumping cavity a distance greater than twice the adjacent wall thickness of the sac pumping chamber 42. The ring is beveled outwardly from the equator 20 and the inner circumferential edge of the ring is rounded to provide a smooth lip 80 located a short distance on the diaphragm side of the equator.

With the exception of the connection between the ends of the inlet and outlet ports and the inlet and outlet valves, sac 40 is positioned freely within the interior of body 12 and the ellipsoidal pumping chamber 42 is closely fitted within but not attached to cavity 18.

The base cover 14 and 16 may be machined from solid polycarbonate plastic. Special care is taken to smooth the interior surfaces which contact the sac or diaphragm. Ring 78 may also be formed from polycarbonate plastic and is smoothed to prevent wear on the diaphragm as it is flexed during pumping.

The sac and diaphragm are preferably fabricated from a plastic material. The segmented polyurethane Biomer, a product marketed by Ethicon, Inc. of Somerville, N.J., may be used. The Biomer product is a partially cross-linked segmented copolymer of tetramethylene glycol and methylene diphenyl isocyanate commercially available in a solution of NN-dimethyl acetamide.

The sac preferably includes a plurality of integrally bonded thin layers of segmented polyurethane. The sac 40 has three continuous inner layers 82 which extend completely around the chamber 42 and the inlet and outlet ports 46 and 48. The sac also includes a number of partial layers 86 of polyurethane. These layers extend around the outlet port 48 and the adjacent inlet port 46 and extend to the immediate portion of the pumping chamber 42 adjacent the outlet port. As illustrated in FIG. 5, the outer partial layers 86 extend further down the body of the chamber 42 than the inner layers 86 with the result that the thickness of the sac is smoothly tapered at the edge or periphery of the partial layers. A single continuous outer layer 88 extends completely around the outer surface of the sac and overlies the outer partial layers 86 and the exposed part of the outermost inner layer 82 not covered by the layers 86.

Layers 82, 86 and 88 each have a thickness of about 0.004 inch so that the thick sac portion 90 made up of eight layers has a thickness of 0.032 inch and the thin portion 92 of the sac 42, comprising the majority of the pumping chamber 42 away from the outlet port, has a thickness of 0.016 inch. A smooth transition ring 94 having a width of about 0.050 inch surrounds the edge of the thick portion 90 to provide a smooth transition between the portions and to distribute stresses during flexing of the sac. As illustrated in FIG. 4, the thick portion 90 extends beyond equator 20 opposite the outlet port 48 and overlies the outlet port.

The layers of the sac are integrally bounded to each other define a unitary, flexible whole. The thin sac portion 92 is more easily flexed than the thicker portion 90. The continuous inner surface of layer 82 contacts the blood during pumping. In order to assure long survival rates, it is essential that this surface be hemocompatible to avoid thrombus formation. Hemocompatibility is assured by making the surface sufficiently smooth to be free of thrombus-forming roughness.

The sac is manufactured by first casting a hollow polyethylene form having an exterior shape conforming to the interior shape of the sac. Polyethylene manufactured by Eastman Chemical Co. of Kingsport, Tenn. Under the trademark EPOLNE C-10 may be used. The form is cast in a machined aluminum mold. Following setting of the form and removal from the mold the exterior surface is sanded to remove the seam line and is coated with a high gloss methylated silicone rubber dispersion. Dispersion No. 236 as marketed by Dow Corning Corporation of Midland, Mich. may be used. This coating operation is perferably performed within a laminar flow hood in order to prevent impurities form being imbedded within the dispersion before it cures. The cured silicone rubber has a highly smooth exterior surface finish.

Dipping is performed within a laminar flow hood. The completed mold is first immersed within a solution of segmented polyurethane to provide an initial layer of polyurethane surrounding the entire form. The dipped mold is removed from the solution and is rotated within the laminar flow hood to dry the first layer by solvent evaporation. Following drying of the initial layer, the entire mold is successively dipped and dryed to provide the desired number of integral layers of segmented polyurethane on the outer surface of the mold. The mold is then inverted and the outlet port and the adjacent area, including the inlet port, are immersed into the solution so that an additional layer of segmented polyurethane is formed on the outlet and inlet ports and extends around the mold adjacent the ports. The mold is dried after each dip. Additional partial layers are formed by repeated dips of this type with successive dips being slightly deeper so that each partial layer covers a slightly greater area of the mold. These partial layers increase the thickness of the sac at the inlet and outlet ports and at an area surrounding the outlet port.

Following dipping, the layers are thoroughly dried and the mold is crushed and removed, leaving the completed sac. The sac is cleaned, sterilized and fitted to the blood pump case.

Referring now to FIGS. 11 and 12, the domed pumping wall 56 of diaphragm 54 includes a thin relatively flexible portion 96 and a thicker relatively less flexible chordal portion 98 separated by a transition strip 100 having decreasing thickness from the thick chordal portion to the thin portion. The pumping wall 56 is domed away from the cylindrical lip 58 and may include mesh or rigid reinforcing at central portion 102 if desired. This reinforcement limits flexing of the diaphragm into the pumping recess 32 at the diastolic position. As illustrated in FIG. 12, the outer sac-contacting surface 106 of the pumping wall is smooth with the transitions strip 100 lying on the inner surface 104.

The diaphragm is preferably fabricated from Biomer segmented polyurethane. An aluminum mold is machined to the figuration of the diaphragm and layers of liquid segmented polyurethane are applied to the mold in the laminar flow hood to provide the desired thickness. The mold is rotated and dried between application of each layer. Three layers of polyurethane are coated over the entire surface of the mold and then three successively smaller layers are coated over the chordal portion 98 to provide the desired extra thickness. A final layer may then be coated over the entire surface of the mold. Following final curing the diaphragm is removed from the mold. The domed surface of the mold defining the final outer surface 106 is highly polished to insure that the surface of the diaphragm contacting the sac is smooth and does not injure the sac.

Blood pump 10 is assembled by positioning sac 40 within the pumping cavity of the base with the inlet and outlet ports extending through the inlet and outlet passages. Suitable inlet and outlet valves are then attached to the necks 22 and 24 to provide fluid flow communication between the interior of the sac and the cannulae 50 and 52 extending from the valves. The valves 28 and 30 may be of conventional design. Valve 30 shown in FIG. 6A is a conventional outlet ball valve. Inlet valve 28 may be of the conventional tilting disc type. This type of valve provides a desirable circulation of blood around the equator of the sac on the inlet or diastolic stroke. Other types of valves may be used, if desired.

The pumping sac 40 conforms to the shape of the pumping chamber 18 and is freely positioned within the chamber but is not physically attached to the chamber. The only connections between the sac and the case occur adjacent to the valves 28 and 30 and are remote from the pumping chamber 42. These connections do not effect the motion of the chamber during pumping.

The diaphragm 54 is mounted on the retaining lip 62 of cap 16 as shown in FIG. 9C with bead 60 in groove 66 and lip 58 resting against the exterior wall 64. The retaining ring 72 is placed in position behind shoulder 76 and, with control ring 78 in position against notch 68 as shown in FIG. 9C lip 62 is pressed against the side of ring 78 with the diaphragm confined there between. The ring 72 is threaded into engagement with cylindrical wall 70 to hold the lip against the ring and form a seal between the diaphragm and the cover of the base. The edge of the diaphragm clamped between the cover and ring is of uniform thickness to assure a tight seal. The interface between the control ring 78 and base 14 is air tight. A suitable lubricant, such as a silicone based grease, is applied to the outer surface 104 of the diaphragm to provide lubricant between the diaphragm and the adjacent surface 108 of sac 40. For purposes of simplicity, some Figures omit the control unit and conduit 38. During operation of the pump the interior of sac 40 is always filled with blood. In the drawings the sac is shown empty in order to simplify the description of the pumping operation.

FIGS. 6A and 6B illustrate pump 10 in the full or diastolic position. A vacuum pulse from control unit 36 has evacuated the pumping chamber 110 between the diaphragm 54 and the adjacent interior surface of the pumping cavity 18 in cover 16. The vacuum pulse is communicated to the chamber 110 through passage 34 to lower the pressure of the chamber below the pressure of the blood in blood chamber 42 so that this chamber is fully expanded. The semiellipsoidal wall 56 of diaphragm 54 and the semiellipsoidal side of the blood chamber 42 adjacent the cover 16 are together in intimate lubricated surface-to-surface contact so that they move together as a single flexible pumping wall 114. The vacuum pulse draws this wall into the semiellipsodial recess of cover 16 to fully expand and fill the blood chamber 42. During the filling operation the inlet valve 28 is open and the outlet valve 30 is closed, as illustrated. Inlet valve 28 may be of the tilting disc type to swirl the inlet flow of blood around the periphery of the chamber 42 to thoroughly mix the blood in the chamber and eliminate stagnation. During filling of the blood chamber the half 116 of the blood chamber 42 fitted within the cavity in the base 14 is maintained in a position adjacent to the walls of the cavity. The blood chamber may be separated a slight distance from the walls of the pumping cavity 18 to define an air pocket 118 separate from the pumping chamber 110. The pocket 118 changes shape during pumping.

The pumping wall 114 in the full diastolic position bridges pumping recess 32. The reinforced portion 102, if provided, aids in strengthening the central portion of the diaphragm to prevent drawing of the wall into the recess. Preferably, the vacuum pulse is adjusted to prevent drawing of the wall into the recess sufficiently to stretch neither the diaphragm or the sac. In this position, the annular portion of the pumping wall outwardly of recess 32 is seated on the interior surface of the pumping cavity defined by cover 16 and the sac extends through and may lightly touch the control ring 78. The sac is separated from the diaphragm for a slight distance on the cover side of the ring and is also separated from the base by air pocket 118 a slight distance from the base side of the ring.

When the sac and diaphragm are in the diastolic position the sac is fully expanded without stress forces and the diaphragm is fully collapsed and preferably free of stress forces. In this position, the sac is completely filled with blood.

After the blood chamber has been completely filled the control unit 36 is reversed to supply a pressure pulse to the pumping chamber 110 thereby increasing the pressure within the chamber and moving the flexible pumping wall 114 from the diastolic position of FIGS. 6A and 6B through the positions of FIGS. 7A and 7B and 8A and 8B to the systolic position of FIGS. 9A, 9B and 9C. The area of the pumping wall 114 is greater than the diametrical cross sectional area of the pumping cavity 18. This means that wall 114 flexes as it is moved across the cavity. The design of the pump controls flexing of the pumping wall to eliminate tensioning of either the sac or diaphragm while, at the same time, improving the flow characteristics of the pump. During flexing of the wall 114 there may be some slight lateral shifting of the diaphragm wall 56 relative to the blood chamber wall 112. The lubricant provided at the interface between these walls assures that this shifting has a minimum effect upon the walls.

Pressurization of chamber 110 initially flexes the wall 114 toward base 14 by forming a dimple or depression in the central portion of the wall at recess 32. The dimple is initially formed in the portion of wall 114 in the thin sac portion 92 and the thin diaphragm portion 96.

Further flexing of the wall 114 expands the dimple beyond the thin wall sections of the sac and diaphragm to the thicker, less flexible portions 90 and 98. The diaphragm is positioned with stiff portion 98 overlying the thick portion 90 of the sac so that the strip 100 overlies the ring 94. The composite thick portion of the pumping wall 114 is less flexible than the composite thin portion of the wall so that the pneumatic pressure exerted against the wall from chamber 110 flexes the thin wall portion toward the base faster than the thick wall portion is flexed toward the base. This means that the dimple expands faster toward the bottom of the pump than it expands toward the top of the pump so that, as illustrated in FIGS. 7A and 7B, the bottom portion 120 of the blood chamber 42 is collapsed prior to collapse of the upper portion 122 of the chamber adjacent the outlet port 48. In this position, the center 124 of the dimple is located well below the diametrical center of the chamber 42 and the blood chamber is more nearly collapsed away from the outlet port.

FIGS. 8A and 8B illustrate the position of the pumping wall 114 following further movement toward the systolic position. In this position the lower portion 120 of the blood chamber have been nearly completely collapsed to complete pumping of blood out of the portion of the sac furtherest away from the outlet port. The dimple has expanded into the thickened wall portions of the blood chamber and diaphragm so that its center 126 has been moved up with respect to the position center 124 in FIG. 7A.

FIGS. 9A and 9B illustrate the pump in the full systolic position with pumping wall 114 fully collapsed. The dimple has expanded to include all of the pumping wall so that the pumping chamber is fully collapsed and the diaphragm is fully extended. The diaphram is flexed 90° around the rounded lip 80 of control ring 78 and the ring holds the diaphragm away from the wall of cavity 18 in base 14 to prevent the interior surfaces of the blood chamber from contacting each other and injuring the blood. The pressure pulse moves the wall 114 to the systolic position and is controlled to prevent stretching of the wall beyond this position.

During the systolic stroke of the pump the thickened portions of the sac and diaphragm on wall 114 prevent premature collapse of the wall to obstruct the output port. With the pump in the normal vertical operating position of FIG. 6A, the weight of the blood in the filled chamber produced a greater hydrostatic pressure at the bottom of the chamber than at the top of the chamber. The pneumatic pressure pulse supplied to the pumping chamber 110 exerts an essentially uniform pressure on the entire wall 114 which is resisted by the hydrostatic pressure. In a blood pump where the pumping wall is uniformally flexible, the upper wall will collapse first followed by progressive collapse down the wall. This means that the top of the wall will move against the outlet port to obstruct passage of blood to and out the outlet port prior to collapse of the bottom of the wall and ejection of the majority of the blood in the chamber.

The thick less-flexible part of the pumping wall 114 resists initial collapse at the top of the chamber due to the hydrostatic pressure gradient and assures that the bottom of the chamber collapses prior to collapse of the top of the chamber. Premature obstruction of the outlet port is avoided.

The thickened sac portion 90 extends along and around the outlet port 48. Blood is pumped out of the outlet port 48 at a sufficiently high flow rate to reduce the pressure at the port. This Venturi effect pressure drop tends to collapse the unattached outlet port and the adjacent part of the chamber to obstruct the port. The increased thickness portion 90 of the sac at the outlet port and the surrounding part of the blood chamber prevents premature collapse of the sac due to these high ejection flow rates.

FIG. 9C is an enlarged view of the lower equatorial portion of pump 10 in the systolic position and is representative of the relationship between the sac, diaphragm and ring at the equator. The diaphragm 54 extends from the cover lip 62 along the flat adjacent side of ring 78 and is bent nearly 90° around the rounded edge of the lip into the pumping cavity of base 14. In this position, the wall 56 is spaced from the adjacent pumping wall cavity 18 a distance greater than twice the thickness of the sac. This space provides room adjacent to the undercut equatorial side of the ring for the annular 180° reverse bend 130 in the sac which connects the two semiellipsoidal sides of the chamber. Portion 130 lies approximately on the equator of the pumping chamber. The ring holds the diaphragm and prevents it from moving sufficiently into the base to bring the inner blood-contacting surfaces of the sac together.

When the diaphragm wall 56 is in the diastolic position it is bent nearly 90° around the cover lip 62 and rests on cover surface 18. This position is illustrated in dotted lines in FIGS. 9C. As the diaphragm is moved back and forth between the two extreme positions the portion adjacent the ring 78 flexes nearly 90° about lip 62 and the portion at the edge of the ring flexes nearly 90° about the lip 80, thereby distributing the almost 180° flexing stresses over two radially spaced portions of the diaphragm. Lips 62 and 80 are rounded to prevent injury to the diaphragm. The spaced double bending of the diaphragm on rounded surfaces distributes stresses throughout of the diaphragm and reduces diaphragm fatigue. This increases the useful life of the diaphragm over that of a diaphragm in a conventional blood pump which flexes back and forth about a single location.

Following pumping of the blood from the chamber past valve 30, the control unit 36 is shifted to supply a vacuum pulse to pumping chamber 110 thereby moving the pumping wall back toward the diastolic position of FIGS. 6A and 6B. The initial movement of the wall back from the systolic position closes the outlet valve and opens the inlet valve. Movement of the pumping wall to the diastolic position and filling the sac is also a function of the atrial or inlet pressure of the blood and the memory molded into the sac walls, particularly the memory of the thick sac wall portion 90 which tends to return the sac to the diastolic position. The diaphragm may also be formed in the diastolic positions, in which case the memory of position 98 also would contribute to returning the wall 114 to the position of FIG. 6A.

After filling of the sac and flexing of the pumping wall back to the position of FIG. 6A, the control unit 36 is again shifted to provide a pressure pulse to chamber 110, thereby initiating the next stroke. The transition ring 94 and transition strip 100 joining the thin and thicker portions of the sac and diaphragm prevent stress formation at the junctions between these two portions during flexing of the pumping wall. In this way, fatigue and cracking of the sac and diaphragm are reduced.

Blood pumps 10 have been surgically attached to calves to provide left ventricle assist and full heart replacement, both as implants and as paracorporeal units. The pumps used in these experiments have a length of 10.2 centimeters, a width of 9.5 centimeters and a thickness of 6 centimeters. Blood chamber 42 has a capacity of 140 milliliters with a static stroke of 118 milliliters. In testing the pump on a closed laboratory loop without atrial back pressure, the pump ejected 118 milliliters with an ejection fraction of 84%. In the calf experiments the pump ejected 105 milliliters of blood per stroke with a dynamic ejection fraction of 75%. In calf experiments the pumps were driven from 70 to 120 beats per minute with a corresponding pumping capacity from 7 to 11.5 liters per minute. The pump control units are programmed to assure that each stroke moves the pumping wall back and forth between the full diastolic and systolic positions to assure a maximum volume of blood is pumped with a minimum number of valve closings. Minimizing the number of valve closings minimizes the inevitable injury to the blood on each valve closing because of physical capture of cells between the valve member and seat. Calf experiments have extended for as long as four months with the pump cycling at 100 beats per minute. One calf lived 100 days with an implanted heart using two pumps.

At the end of each study, the pumps are carefully inspected for damage or thrombus formation. Very little, if any thrombus has been found and the diaphragm and sac are found free of flex cracks or other injury. None of the calves died as a result of pump malfunction. No pump-related injury has been found.

Control unit 36 may be of the conventional type manufactured by Vitamek, Inc. of Houston, Tex. This unit includes a pressure and vacuum pulser and a timing unit. A synchronizing unit may be used to actuate the pulser in response to the R wave of the patient's electrocardiogram.

While blood pump 10 has been described as being driven by a pneumatic pressure and vacuum pulses, it is intended that a sac may be driven by a mechanical drive connected to the diaphragm to move the diaphragm back and forth between the diastolic and systolic positions. In this case, the central portion 102 of the diaphragm would be inflexible and would be connected to a linear operator to move the diaphragm back and forth. The operator may be a small electrical motor carried by the cover and receiving power from an external source.

While we have illustrated and described the preferred embodiment of our invention, it is understood that this is capable of modification, and we therefore do not wish to be limited to the precise details set forth, but desire to avail ourselves of such changes and alterations as fall within the purview of the following claims.

What we claim as our invention is:

1. A blood pump comprising a case defining a pumping cavity, inlet and outlet passages leading into the cavity; a thin walled pumping sac comprising a pumping chamber positioned freely within the cavity and integral inlet and outlet ports positioned within the inlet and outlet passages, the chamber including first and second parts and an equator joining the parts with the outlet port formed in the first part adjacent the equator; inlet and outlet valves on the case at the ends of the inlet and outlet passages connected in a fluid flow relation to said inlet and outlet ports for controlling the flow of blood through the pump; means for alternately expanding and collapsing the second part of the chamber to pump blood past the valves, a portion of the pumping sac adjacent to the outlet port having a greater resistance to flexing than the remainder of the chamber, said portion extending across the equator and overlying the outlet port, whereby during pumping of blood from the chamber the portion collapses subsequent to collapse of the remainder of the chamber.

2. A blood pump as in claim 1 wherein the outlet port is positioned freely within the outlet passage and the outlet port has a greater resistance of flexing than the remainder of the chamber to resist Venturi effect collapse during pumping of blood from the chamber.

3. A blood pump as in claim 2 including means for limiting collapse of the pumping chamber to prevent touching of the interior surfaces thereof.

4. A blood pump as in claim 3 wherein the pumping cavity and pumping chamber are both ellipsoidal in shape and have essentially co-planar equators, and said inlet and outlet ports are located adjacent to each other and close to and on one side of the chamber equator.

5. A blood pump as in claim 4 wherein said means includes a generally semiellipsodal diaphragm attached to the case and extending into the pumping cavity adjacent the equator, the diaphragm and the adjacent side of the chamber engaging each other to form a flexible pumping wall, lubricant on the interface of the pumping wall between the diaphragm and the side of the pumping chamber, and means for communicating pressure and vacuum pulses to the chamber between the diaphragm and the side of the pumping cavity away from the pumping chamber.

6. A blood pump as in claim 1 wherein the outlet port and the portion of the sac adjacent the outlet port are thicker than the remainder of the chamber.

7. A blood pump as in claim 6 wherein the sac comprises a number of integrally bonded layers of a flexible material, the inner surface of the sac being defined by a single continuous layer, the outer surface of the sac being defined by a second continuous layer and the less flexible portions of the sac being formed by at least one partial layer lying between the continuous inner and outer layers.

8. A blood pump as in claim 1 wherein the pumping chamber, when expanded, has an equator separating a pair of like chamber sides, said inlet and outlet ports being located on one side of the chamber, and including a control ring extending around the periphery of the pumping cavity on the side of the equator away from the inlet and outlet passages, and a pumping diaphragm attached to the case adjacent the side of the control ring away from the equator and generally conforming to the shape of the adjacent side of the pumping chamber, means for introducing pressure and vacuum pulses into the space between the diaphragm and adjacent wall of the cavity away from the chamber so that the diaphragm and adjacent side of the chamber move together between the expanded and collapsed positions of the chamber with the diaphragm being flexed over the inner edge of the ring when the chamber is collapsed and being flexed about its attachment to the case when the chamber is expanded.

9. A blood pump as in claim 8 wherein the ring extends into the cavity a distance greater than twice the thickness of the sac wall at its equator.

10. A blood pump comprising a case defining a pumping cavity with inlet and outlet passages, a thin walled pumping sac freely positioned within the case with a pumping chamber in the pumping cavity and inlet and outlet ports in the inlet and outlet passages, inlet and outlet valves at the ends of the passages in fluid flow communication with the inlet and outlet ports, the pumping chamber having two like sides separated by an equator, said inlet and outlet ports being located adjacent to each other and close to and on one side of the equator, means for flexing a first side of the pumping chamber away from the inlet and outlet ports between extended and collapsed positions about a smooth generally equatorial flex line to pump blood into and out ot the sac, and means within the cavity for preventing the interior surfaces of the sides from touching each other when the chamber is collapsed.

11. A blood pump as in claim 10 including means operable during collapse of the pumping chamber for moving the portion of said first side away from the outlet port toward the other side faster than the remainder of the first side is moved toward the outlet port.

12. A blood pump as in claim 10 wherein the pumping cavity and pumping chamber are both ellipsoidal in shape and have essentially co-planar equators.

13. A blood pump as in claim 10 wherein the outlet port and the portion of the sac surrounding and overlying the outlet port are less flexible than the remainder of the chamber.

14. A blood pump as in claim 13 wherein the sac comprises a number of integrally bonded layers of a flexible material, the inner surface of the sac being defined by a single continuous layer.

15. A blood pump as in claim 10 including a control ring extending around the pumping cavity on the side of the equator away from the inlet and outlet ports, and a pumping diaphragm attached to the case at the side of the control ring away from the equator and generally conforming to the shape of the adjacent side of the pumping chamber, means for introducing pressure and vacuum pulses into the space between the diaphragm and adjacent wall of the cavity away from the chamber so that the diaphragm and adjacent side of the chamber move together between the expanded and collapsed positions of the chamber with the diaphragm being flexed over the inner edge of the ring when the chamber is collapsed and being flexed about its attachment to the case when the chamber is expanded.

16. A blood pump as in claim 15 wherein the ring extends into the cavity a distance greater than twice the thickness of the adjacent sac wall.

17. A blood pump comprising a case defining a pumping cavity, inlet and outlet passages leading into the cavity, a thin walled pumping sac comprising a pumping chamber positioned freely within the cavity with integral inlet and outlet ports positioned within the inlet and outlet passages, inlet and outlet valves on the case at the ends of the inlet and outlet passages connected in fluid flow relation to said inlet and outlet ports for control flowing of blood through the pump, the pumping chamber having an equator separating first and second like sides with the inlet and outlet ports joining the second side, a diaphragm generally conforming in shape to the first side attached to the case and extending across the cavity, said diaphragm engaging the outer surface of said first side to form a unitary pumping wall, a control ring projecting into the cavity and extending around the cavity between the equator of the chamber and the diaphragm, and means for moving the pumping wall back and forth to expand and collapse the pumping chamber and pump blood past the valves, whereby upon collapse of the pumping wall the control ring prevents the interior surfaces of the chamber sides from touching each other.

18. A blood pump as in claim 17 wherein the control ring extends into the cavity a distance greater than twice the thickness of the adjacent sac wall.

19. A blood pump as in claim 17 wherein a first portion of the pumping chamber surrounding the outlet port is less flexible than the remainder of the pumping chamber away from the outlet port.

20. A blood pump as in claim 19 wherein the inlet and outlet ports are adjacent to each other and are adjacent the pumping chamber equator, and said first portion extends across the chamber equator and overlies the outlet port.

21. A blood pump as in claim 20 wherein the outlet port is less flexible than the remainder of the pumping chamber.

22. A blood pump as in claim 17 wherein the inner edge of said ring is rounded to form a smooth lip and the diaphragm extends from the inner surface of the cavity on the side of the ring away from the equator so that the diaphragm flexes about two radially spaced flex areas as the pumping wall is moved between the systolic and diastolic positions.

23. An improved blood pumping sac adapted to be positioned freely within the case of a blood pump, said sac being formed of a thin, flexible and appendage free material with a hemocompatible inner surface, the sac comprising a pumping chamber with an equator, two like sides separated by the equator, and integral inlet and outlet ports in one side, the outlet port being located adjacent the equator, the sac including a less flexible portion surrounding the outlet port, extending across the equator to the other side and overlying the outlet port to resist premature collapse during pumping of blood from the chamber.

24. An improved blood pumping sac as in claim 23 wherein the less flexible portion of the chamber is thicker than the remainder of the chamber.

25. An improved blood pumping sac as in claim 24 wherein the sac comprises a number of integrally bonded layers of a flexible material, the inner surface of the sac being defined by a single continuous layer and the less flexible portion of the chamber including at least one additional partial layer.

26. An improved blood pumping sac as in claim 25 wherein the outer surface of the sac is defined by a single continuous layer of the flexible material.

27. An improved blood pumping sac as in claim 26 including a tapered transition portion surrounding the thicker portion of the chamber.

28. An improved blood pumping sac as in claim 26 wherein the pumping chamber is generally ellipsoidal and the inlet and outlet ports are located adjacent to each other and adjacent to the equator.

29. A blood pump comprising a case defining a pumping cavity and inlet and outlet passages leading into the cavity; a thin-walled pumping sac comprising a pumping chamber positioned freely within the cavity with integral inlet and outlet ports positioned within the inlet and outlet passages, the pumping chamber, when expanded, having an equator separating a pair of like chamber sides, said inlet and outlet ports being located on one of the chamber sides; a control ring unitary with the case extending around the periphery of the pumping cavity on the side of the equator away from the inlet and outlet passages; a pumping diaphragm attached to the case adjacent to the side of the control ring away from the equator and generally conforming to the shape of and lying on the adjacent chamber side of the pumping chamber to form a flexible pumping wall; inlet and outlet valves on the case at the ends of inlet and outlet passages connected in fluid flow relation to said inlet and outlet ports for controlling the flow of blood through the pump; and means for introducing pulses into the space between the diaphragm and adjacent wall of the cavity away from the chamber so that the diaphragm and adjacent side of the chamber move together between expanded and collapsed positions of the chamber with the diaphragm flexed over the inner edge of the ring when the chamber is collapsed and being flexed about its attachment to the case when the chamber is expanded.

30. A blood pump comprising a case defining a pumping cavity having a cavity equator separating a pair of generally like cavity sides, inlet and outlet passages leading into the cavity, said passages being located on one side of the cavity equator; a thin-walled pumping sac comprising a pumping chamber positioned freely within the cavity with integral inlet and outlet ports positioned within the inlet and outlet passages, said sac having an equator substantially coincident with the cavity equator; inlet and outlet valves on the case at the ends of the inlet and outlet ports for controlling the flow of blood through the pump; the case including a control member extending into the pumping cavity on the other side of the cavity equator and extending at least partially along such equator; a pumping diaphragm attached to the case on the other side of the cavity equator with the control member located between the diaphragm and the cavity equator, the diaphragm generally conforming in shape to the shape of and lying on the adjacent side of the pumping chamber to form a flexible pumping wall; and means adaptable for moving the pumping wall between expanded and collapsed positions of the chamber with the diaphragm being flexed over the inner edge of the control member when the chamber is collapsed and being flexed about its attachment to the case when the chamber is expanded.

31. A blood pump as in claim 30 wherein said control member includes a control ring extending around the cavity.

32. A blood pump as in claim 30 where the sac includes a relatively less-flexible portion including said inlet and outlet ports and a relatively more flexible portion comprising the remainder of the pumping chamber, said relatively less-flexible portion extending from said inlet and outlet passages across the sac equator and overlying the outlet passage so as to resist flexing into the passage during movement of the sac to the collapsed position.

33. An improved pumping diaphragm for use in blood pump, said diaphragm including a thin domed flexible wall adapted to be moved between extended and retracted positions, and means on the periphery of the wall for attaching the diaphragm to the case of a blood pump, said wall including a peripheral portion having greater resistance to flexing than the remainder of the wall.

34. An improved pumping diaphragm as in claim 33 wherein the peripheral portion is thicker than the remainder of the wall and including a smooth transition portion joining the peripheral portion and remainder of the wall.

35. An improved pumping diaphragm as in claim 33 wherein said peripheral portion is chordal.

36. The method of pumping blood using a collapsible sac having a thin walled flexible pumping side and a nonmoving side with inlet and outlet ports extending from the nonmoving side and with the outlet port located adjacent to the edge of the pumping side, comprising the steps of:
   A. Expanding the sac to fill the sac with blood flowing through the inlet port by moving the pumping side away from the nonmoving side; and then
   B. Collapsing the sac to pump blood out the outlet port without obstruction by moving the portion of the pumping side remote from the outlet port toward the nonmoving side faster than the portion of the pumping side overlying the outlet port is moved toward the nonmoving side and completing collapse of the pumping side remote from the outlet port prior to restriction of the outlet port by collapse of the portion of the pumping side overlying the outlet port.

37. The method of claim 36 including the step of forming an initial depression in the pumping side of the sac remote from the outlet port and then radially expanding the depression while collapsing the pumping side to move the pumping side smoothly from the expanded to the collapsed positions.

38. The method of claim 37 including the step of expending the depression in a direction toward the outlet port slower than it is expanded in a direction away from the outlet port.

39. The method of claim 38 including the step of expanding the depression to a smooth crease-free 180° bend at the junction between the sides when the sac is fully collapsed.

40. The method of claim 39 including the step of preventing touching of the inner surfaces of the two sides while pumping.

41. The method of pumping blood using a pump having a flexible pumping chamber and a flexible diaphragm peripherally secured to the pump overlying one side of the chamber, comprising the steps of:
   A. Moving the diaphragm through a diastolic stroke to expand and fill the chamber;
   B. Moving the diaphragm through a systolic stroke to collapse and empty the chamber; and
   C. During each diastolic and systolic stroke successively flexing the diaphragm at its periphery about each of a pair of spaced peripheral flex areas.

42. The method of claim 41 including steps of:
   D. Flexing the diaphragm during each diastolic stroke first about an outer peripheral flex area and then about an inner peripheral flex area; and
   E. Flexing the diaphragm during each systolic stroke first about the inner peripheral flex area and then about the outer peripheral flex area.

43. The method of claim 42 including the step during each stroke of flexing the diaphragm approximately 90° about each of the inner and outer peripheral flex areas.

* * * * *